United States Patent
Yura et al.

(10) Patent No.: US 6,926,915 B1
(45) Date of Patent: Aug. 9, 2005

(54) METHOD FOR SELECTIVELY SEPARATING BLOOD CELLS BY USING LECTIN

(75) Inventors: Hirofumi Yura, Kawasaki (JP); Yoshio Saito, Yokohama (JP); Michihiro Kitagawa, Tokyo (JP); Daisuke Wakamatsu, Kobe (JP); Akira Ihara, Tokyo (JP)

(73) Assignee: Netech, Inc., Kanagawa (JP)

( * ) Notice: Subject to any disclaimer, the term of this patent is extended or adjusted under 35 U.S.C. 154(b) by 0 days.

(21) Appl. No.: 09/937,510

(22) PCT Filed: Mar. 30, 2000

(86) PCT No.: PCT/JP00/02011

§ 371 (c)(1),
(2), (4) Date: Jan. 23, 2002

(87) PCT Pub. No.: WO00/58443

PCT Pub. Date: Oct. 5, 2000

(30) Foreign Application Priority Data

Mar. 30, 1999  (JP) .......................................... 11-090256

(51) Int. Cl.$^7$ .............................................. A61K 35/78
(52) U.S. Cl. ...................................... 424/757; 424/725
(58) Field of Search .................................. 424/725, 757

(56) References Cited

FOREIGN PATENT DOCUMENTS

| | | |
|---|---|---|
| JP | 8-319300 | 12/1996 |
| WO | WO 97/26326 | 7/1997 |
| WO | WO 99/15628 | 4/1999 |

OTHER PUBLICATIONS

Tatsuya Sato et al., "An Efficient Method of Bone Marrow Transplantation II. Design of Absorbent Column for Depletion of T Lymphocytes and Concentration of Stem Cells from Donor Bone Marrow", Journal of Tokyo Jikeikai Ika Daigaku, 1996, vol. 11, No. 1, p. 9–18.

Arnon Nagler, et al., "The Use of Soybean Agglutinin (SBA) for Bone Marrow (BM) Purging and Hematopoietic Progenitor Cell Enrichment in Clinical Bone–Marrow Transplantation", Molecular Biotechnology, Apr. 1999, vol. 11, No. 2, p. 181–194.

Miercio E. A. Pereira and Elvin A. Kabat, "Immunochemical Studies on Lectins and Their Application to the Fractionation of Blood Group Substances and Cells", Critical Reviews in Immunology, Nov., 1979, pp. 33–78.

M. Kitagawa, K. Sugiura, T. Okuyama, K. Kanayama, M. Natori, D. Wakamatsu, H. Yura and H. Sago, "A New Method Using Lectin for Isolation of Fetal Cells from Maternal Blood", American Journal of Human Genetics, Oct. 2000, p. 423.

Michihiro Kitagawa, Kentaro Sugiura, Hiroko Omi, Yoshiaki Akiyama, Kiyoko Kanayama, Masaru Shinya, Tadao Tanaka, Hirobumi Yura and Haruhiko Sago, "New Technique Using Galactose–Specific Lectin for Isolation of Fetal Cells from Maternal Blood", Prenatal Diagnosis, Jan. 2002, pp. 17–21.

*Primary Examiner*—Jean C. Witz
(74) *Attorney, Agent, or Firm*—Pearne & Gordon LLP

(57) ABSTRACT

The present invention provides a method for selective and high-yield separation, concentration, and recovery of desired cells from a blood sample. The method of the present invention is characterized in that the blood sample is caused to interact with lectins under conditions in which the cell membranes are inactive and cell-lectin complexes/non-complexes are formed, the sample containing these cell-lectin complexes/non-complexes is incubated together with a substrate, the surface of which is covered with polymers having carbohydrate chains which are specifically recognized by the lectins, and the cells are immobilized on the surface of the substrate via the lectins, and subsequently, the liquid layer and the solid phase are separated, and the desired blood cells are recovered from the liquid phase and/or the solid phase, and these lectins are in such an amount that although the cells to be recovered from the solid phase bind to the solid phase with the polymer, the cells to be recovered from the liquid phase do not bind to the solid phase with the polymer.

6 Claims, 2 Drawing Sheets

METHOD FOR SELECTIVELY SEPARATING BLOOD CELLS BY USING LECTIN

FIELD OF THE INVENTION

The present invention relates to a method for the separation of blood cells using lectins, and in particular, relates to a method for the selective separation and recovery of desired blood cells, via lectin, from a sample containing both mature cells and immature cells contained in peripheral blood, bone marrow fluid, umbilical cord blood, or the like.

BACKGROUND OF THE INVENTION

Hematopoietic stem cells are cells which combine the potential of multi-differentiation and autoreproduction. The potential of autoreproduction is most important for hematopoiesis in order that blood cells not become exhausted over the course of a lifetime. With respect to the ability of the hematopoietic stem cells to multi-differentiate, as shown in FIG. 1, stem cells differentiate into myeloid stem cells and lymphatic stem cells, and these further differentiate into platelets, (mature) erythrocytes, granulocytes, monocytes, or the like from the myeloid stem cells, while blood cells such as T cells or B cells or the like are produced from the lymphatic stem cells.

Blood cells have a lifetime and are consumed in accordance with a variety of physiological needs, so that it is necessary that the blood cells be appropriately replenished by differentiation from stem cells. In patients suffering from, for example, acute myelogenous leukemia, there are irregularities in the differentiated functional blood cells themselves, as well as in the stem cell differentiation, so that the replenishment of functional red blood cells, white blood cells, platelets and the like is difficult. The transplantation of hematopoietic stem cells offers a treatment method for such blood diseases which does not have the side effects of chemotherapy and results in the recovery of functional hematopoiesis through the differentiation and regeneration of these cells. However, despite these advantages, the acquisition of stem cells is difficult, as they are almost all distributed in the bone marrow. Although placental blood and umbilical cord blood are comparatively enriched in stem cells, so that a less invasive method of obtaining them is possible, they can be used only in childbirth. On the other hand, in the peripheral blood which can be obtained from a donor in the least invasive way, the amounts of stem cells are further reduced which makes the peripheral blood less practical.

Furthermore, in transplanted blood cells containing stem cells, immunological rejection reaction, termed graft-versus-host disease (GVHD), may be induced when the HLA type of the patient and donor do not match. Accordingly, in order to conduct effective and safe transplantation of stem cells, it is necessary to obtain a stem cell sample from which lymphocyte fractions which give rise to GVHD are removed.

Furthermore, if pure stem cells could be isolated, they could be effectively stimulated and expanded using cytokines. Consequently, stem cell isolation could contribute to the development of stem cell banks in which such cells were stored for later use.

On the other hand, in concert with the recent development in genetic manipulation techniques, efforts have been made to conduct prenatal gene diagnosis for fetal nucleated cells. Fetal nucleated cells for diagnostic use which are currently clinically employed, are collected through invasive methods such as amniocentesis, chorionic villous sampling, and fetal blood collection, and these carry the risk of infection and amniorrhexis. It is conventionally known that fetal cells are admixed in the maternal blood, and the use of maternal peripheral blood to obtain fetal nucleated cells as a noninvasive collection has been considered; however, nucleated red blood cells (NRBC) being likely fetal cells are contained in the maternal peripheral blood in very small amounts, being only 1 in $10^5$–$10^7$ of the total nucleated cells in the peripheral blood, so that the key to genetic diagnosis of fetal cells has been how to concentrate, separate, or identify such cells.

In addition, it is known that gene diagnosis is effective for the therapy of leukemia For example, since leukemia includes various types such as myeloid type in which hematopoietic cells themselves are pathologic or other type in which peripheral lymphocytes or monocytes become malignant, it is necessary to identify the type of leukemia for determining optimal dosing or therapeutic regimen. Moreover, genetic examination is needed to know the stage of differentiation of blood cells in which a carcinogenic factor is induced because the detection of the stage in which carcinogenic cells occur would contribute not only to the treatment of leukemia but also to clinically important matters such as prevention or recurrence of cancer. In such an examination of leukemia, it is also necessary to simplify and make effective the gene diagnosis in each differentiation stage by selecting and purifying immature hematopoietic blood cells and proliferating and differentiating them with cytokines.

The present inventors have conducted research which focused on the specific interactions between carbohydrates and other biological substances, and have filed a patent application on a method for selectively binding lectins, carbohydrate-specific proteins, to a solid support, such as a dish or the like, covered with synthetic glycoconjugate polymers including carbohydrate moieties (Japanese Patent Application No. Hei 8-59695).

On the other hand, as is shown in FIG. 1, hematocytes derived from hematopoietic stem cells express a variety of carbohydrate chains on the cell surface in accordance with the maturation thereof. In FIG. 1, the designation "Gal" indicates galactose, "Glu" indicates glucose, and "Lac" indicates lactose (Glu-Gal). In the patent application referred to above, it is disclosed that mature human erythrocytes expressing galactose are preferentially attached to the surface of the substrate covered with the glycoconjugate polymer including galactose, via a lectin (Allo-A) which recognizes galactose.

The present inventors have now thoroughly explored a control method for blood cell immobilization on a solid support covered with glycoconjugate polymers via lectins, and have discovered that by means of the incubation temperature or the amount of lectins added, a specific system of interactions among the cells and/or the carbohydrate moieties in the polymers and the lectins can be produced; the present invention was arrived at on this basis.

SUMMARY OF THE INVENTION

It is an object of the present invention to provide a method by which desired immature blood cells or differentiated mature cells may be selectively, and with high yield, separated, concentrated, and recovered, using lectins, and to provide a separation apparatus employing this method.

This object can be accomplished by a method for selectively separating and recovering hematopoietic cells and/or erythroblasts from a blood sample containing differentiated mature cells, immature hematopoietic cells and erythroblasts, characterized in that the method comprises the following steps:

(1) a step for causing said sample to interact with lectins to form cell-lectin complexes/non-complexes under conditions in which the cells are rendered inactive, (2) a step for incubating a sample containing said cell-lectin complexes/non-complexes under said conditions with a substrate, the surface of which is covered with a synthetic glycoconjugate polymer having carbohydrate moieties specifically recognized by said lectins, and immobilizing said cells on the surface of said substrate via lectins, and (3) a step for separating the liquid phase from the solid phase, and recovering desired blood cells from said liquid phase and/or said solid phase; and optionally (4) a step for accelerating and stabilizing the immobilization of cells by centrifuging said substrate and cells simultaneously prior to or after the incubation or a step for stabilizing the immobilization of cells by centrifuging the substrate on which the cells are immobilized during the recovering step, and in that said lectins are present in an amount such that they bind to the cells recovered from said solid phase and immobilize these cells on the surface of the substrate, but do not immobilize the cells recovered from said liquid phase to the surface of said substrate.

In the method for selectively separating, the conditions under which the cells are rendered inactive may be low temperature conditions of 0° C. or above but less than 37° C., or conditions in which a pharmaceutical agent is added which suspends cellular respiration. Furthermore, by adjusting the lectin concentration or incubation time, it becomes possible to obtain high-level selective separation which has not been accomplished until now.

Furthermore, the present invention also provides an apparatus for use in the above-described selectively separating method.

The separating method and apparatus of the present invention are based on cell-lectin and glycoconjugate-lectin interactions, and make it possible to selectively separate cells, in particular specific cells having clinically important significance such as hematopoietic cells or NRBC.

DETAILED DESCRIPTIONS FOR PREFERRED EMBODIMENTS

Hereinbelow, the present invention will be discussed in detail.

In the separation method of the present invention, as a first stage, a sample containing cells which are to be immobilized in a solid phase is caused to interact with lectins which recognize carbohydrates expressed on these cells, and cell-lectin complexes/non-complexes are formed. Here, what is meant by cell-lectin complexes/non-complexes is a coexistent state in which both complexes in which cells and lectins are bound to one another, and free and unbound cells and lectins (non-complexes) are present. This step is conducted under conditions such that the cells are rendered inactive.

Here, what is meant by conditions in which the cells are inactive are conditions in which the mobility of the cell membranes and the self-adhesiveness thereof are lowered, and such conditions are typically achieved by adjusting the temperatures to within a range of from 0° C. to less than 37° C., preferably within a range of 0–36° C., more preferably within a range of 4–30° C., and most preferably within a range of 4–22° C. However, these conditions are not necessarily limited to the low temperature adjustment described above; such conditions may also be achieved by, for example, adding a pharmaceutical agent which suspends cellular respiration at 37° C., such as sodium azide or the like.

Figure 1:
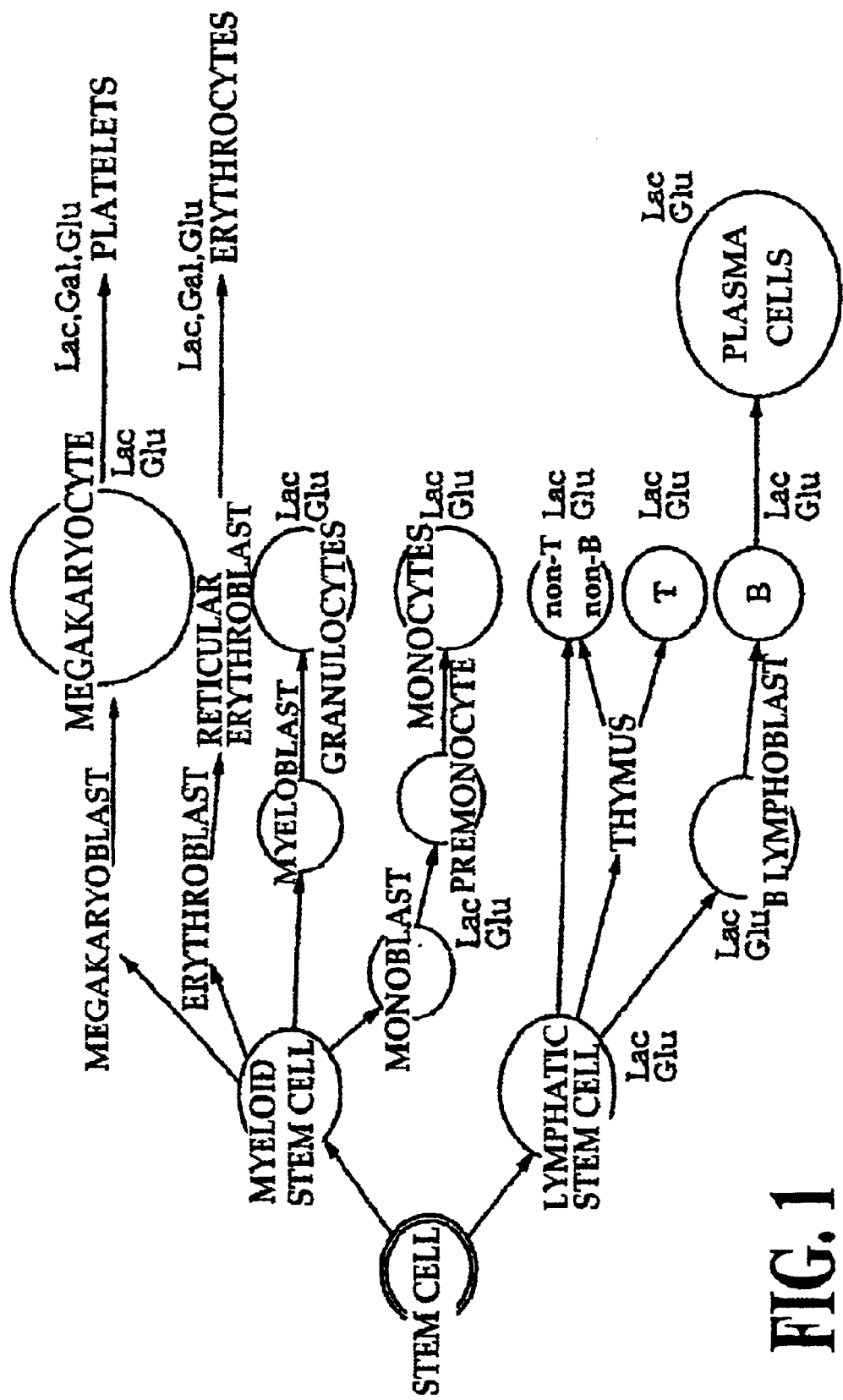
FIG. 1 is a systematic diagram showing the state of hematopoietic stem cell differentiation.

The lectins are employed to recognize carbohydrates expressed on cells, which are to be immobilized. For example, as is shown in FIG. 1, when mature leukocytes, platelets, or erythrocytes of the peripheral blood which express galactose or glucose are to be immobilized, then lectins which recognize galactose, such as SBA, PNA, ECL, Allo A, VAA, or the like, or lectins which recognize glucose such as Con A, LcH, PSA, or the like, are selected. When cells expressing mannose are to be immobilized, then lectins which recognize mannose, such as LCA, GNA, CPA, or the like, are selected.

The amount of such lectins added varies based on the type of cells which are to be immobilized; fundamentally, the amount should be such that, in the following second stage incubation, the cells which are to be immobilized (the cells which are later to be recovered from the solid phase) are bonded to the surface of the substrate covered with the polymers, while the cells which are not to be immobilized (the cells which are later to be recovered from the liquid phase) are not bonded to the surface of the substrate. By means of specifying the amount of lectin added, it is possible to control, for example, the selectivity with respect to the maturity of the cells such as leukocytes or the like, or the selectivity among cell types such as leukocytes, erythrocytes, and the like. Concretely, the concentration is adjusted to 20 mg/ml or less with respect to one cell or more. This amount added varies based on the type of lectins as well, so that for example, when SBA is employed as the lectin, an amount of 5 mg/ml is sufficient.

In particular, when a polymer including a lactose structure, which has a β-bond galactose terminal, or a mellibiose structure, which has an α-bond galactose terminal, is employed as the glycoconjugate polymer, and when CD34-negative mature cells are to be predominantly immobilized with controlling the immobilization of immature CD34-positive cells, the concentration of lectin added with respect to a sample containing $2\times10^6$ cells may be within a range of 0.001–0.9 mg/ml, preferably within a range of 0.002–0.1 mg/ml, and more preferably within a range of 0.025–0.05 mg/ml. Furthermore, when red blood cell (NRBC) are to be selectively immobilized, and other cells such as leukocytes or the like are not to be immobilized, then the concentration of lectin with respect to a sample containing $2\times10^6$ cells may be within a range of 0.001–0.3 mg/ml, preferably within a range of 0.002–0.05 mg/ml, and more preferably within a range of 0.004–0.025 mg/ml.

The incubation period in the first stage is not particularly restricted; it should be set so that the cells and the lectins interact prior to the following second stage, and form cell-lectin complexes/non-complexes, and typically this will be within a range of 0–120 minutes, preferably within a range of 0–90 minutes, and more preferably within a range of 0–60 minutes. Here, what is meant by "0 minutes" is a transfer to the second stage immediately after conducting the first stage. As a result, the cells which are to be immobilized and the lectins form cell-lectin complexes/non-complexes.

Next, as a second stage in the separation method of the present invention, the sample containing the cell-lectin complexes/non-complexes described above is incubated, under ail conditions in which the cells are inactive, on a substrate, the surface of which is covered with the glycoconjugate polymers having carbohydrates which are specifically recognized by the lectins The substrate employed here may be selected from substrates conventionally employed for cell cultivation, such as dishes, flasks, plates, cuvettes, films, fibers, beads, separable chamber slides, or the like; it is possible to use substrates having a variety of shapes depending on the use.

This substrate may be made of inorganic materials such as glass, silica, or the like, or organic materials such as polystyrene, polycarbonate, polysulfone, polyurethane, vinyl copolymers, or the like, as well as composite materials formed therefrom; however, a material which is resistant to the degree of heat required for sterilization and which is water-resistant is preferably used. In particular, synthetic polymeric materials are preferable from the point of view of cost and moldability, and hydrophilic materials are preferable from the point of view of the covering effectively of the glycoconjugate polymers. When, for example, a glycoconjugate polymer containing a main chain made of polystyrene or its derivatives is employed, the use of a substrate material having polystyrene or its derivatives is preferable for the cover.

The surface of the substrate described above is covered with the glycoconjugate polymers having carbohydrate moieties, which are specifically recognized by the lectins used in the first stage.

Examples of such polymers include the following:

Poly(N-p-vinyl benzyl-[O-$\beta$-D-galactopyranosyl-(1→4)-D-gluconamide]) having $\beta$-galactose residues obtained by polymerizing monomers synthesized from p-amino methyl styrene and lactose (referred to as PVLA);

Poly(N-p-vinyl benzyl-[O-$\alpha$-D-glucopyranosyl-(1→4)-D-gluconamide]) having glucose residues obtained by polymerizing monomers synthesized from p-amino methyl styrene and maltose (referred to as PVMA);

Poly(N-p-vinyl benzyl-[O-$\beta$-D-mannopyranosyl-(1→4)-D-mannamide]) having mannose residues obtained by polymerizing monomers synthesized from p-amino methyl styrene and mannobiose (referred to as PVMan);

Poly(N-p-vinyl benzyl-[O-$\alpha$-D-galactopyranosyl-1$\alpha$→6)-D-gluconamide]) having $\alpha$-galactose residues obtained by the polymerization of monomers synthesized from p-amino methyl styrene and O-$\alpha$-D-galactopyranosyl-(1→6)-D-glucose (referred to as PVMeA);

Poly(N-p-vinyl benzyl-[O-6-carboxymethyl-$\beta$-D-galactopyranosyl-(1→4)-O-D-6-carboxymethyl-gluconamide]) having carboxymethylated-$\beta$-galactose residues obtained by the carboxymethylation of PVLA which is obtained by the polymerization of monomers synthesized from p-amino methyl styrene and lactose (referred to as PVLACOOH);

Poly(3-O-4'-vinyl benzyl-D-glucose) having glucose residues obtained by the polymerization of monomers synthesized from p-chloromethyl styrene and glucose (referred to as PVG);

Poly(N-p-vinyl benzyl-[O-2-acetamide-2-deoxy-$\beta$-D-glucopyranosyl-(1→4)-O-D-2-acetamide-2-deoxy-$\beta$-D-glucopyranosyl-(1→4)-O-D-2-acetamide-2-deoxy-$\beta$-D-gluconamide]), poly(N-p-vinyl benzyl-[O-D-2-acetamide-2-deoxy-$\beta$-D-glucopyranosyl-(1→4)-O-D-2-acetamide-2-deoxy-$\beta$-D-gluconamide]) and mixtures thereof having N-acetylglucosamine residues obtained by the polymerization of monomers synthesized from p-chloromethyl styrene and N-acetylglucosamine (all termed PVGlcNac); and Poly(N-p-vinyl benzyl-[O-$\beta$-D-glucopyranosyl-(1→3)-D-gluconamide]) having $\beta$1→3 glucose residues obtained by polymerizing monomers synthesized from p-amino methyl styrene and laminaribiose (termed PVLam).

These glycoconjugate polymers may be homopolymers as described above or may be copolymers with other monomers. For example, copolymers with monomers having azide groups, which are photoreactive functional groups, are preferable in that they facilitate the formation of a covalent bond with the substrate surface by means of the application of light. Examples of glycoconjugate polymers into which azide groups are introduced include: poly(3-azide styrene-co-{N-p-vinyl benzyl-[O-$\beta$-D-galactopyranosyl-(1→4)-D-gluconamide]}), which is a copolymer with the PVLA described above (termed AZ-PVLA); and poly(3-azide styrene-co-{N-p-vinyl benzyl-[O-$\alpha$-D-glucopyranosyl-(1→4)-D-gluconamide]}), which is a copolymer with the PVMA described above (referred to as AZ-PVMA), and the like.

When the incubation in the second stage is conducted in a dish or flask used for cell culturing under the conditions same as described for the first stage above, then the incubation period is typically within a range of 10–120 minutes, preferably within a range of 20–90 minutes, and more preferably within a range of 30–70 minutes. As a result, the cell-lectin complexes to be immobilized are attached to the substrate via the glycoconjugate polymers on the surface of the substrate.

On the other hand, under conditions in which the cell precipitation period can be ignored in a column filled with beads or non-woven fabric, this period may be further shortened. The shortening of the period can also be attained by acceleration and stabilization of the precipitation and immobilization of cells by means of centrifuging the substrate and cells simultaneously prior to or after the incubation of the second stage. The centrifuging period is sufficient within a range of 30 minutes or less, and it preferably be 10 minutes or less from the point of view of shortening time. The centrifuging force will vary depending on the type of cells to be immobilized or types or concentrations of lectins used, and in general it preferably be in a range of 30–450 G.

Next, as a third stage of the separation method of the present invention, the solid phase which is immobilized on the substrate, and the liquid phase which remains unimmobilized are separated. In the case in which a column filled with beads or plates covered with the carbohydrates is employed, a sample containing the cell-lectin complexes/non-complexes obtained in the first stage may simply be introduced into the column, and thereby, it is possible to separate the solid phase by recovering the liquid phase from the outlet of the column.

When chromosomes of the cells attached on a substrate, such as a chamber slide or dish, are examined, the liquid phase staying unattached in the above recovering step is removed, and the substrate on which cells are attached is then centrifuged to stabilize the immobilization of the cells which results in a uniform immobilized image. The centrifuging period is sufficient within a range of 30 minutes or less, and it preferably be 10 minutes or less from the point of view of shortening time. The centrifuging force will vary depending on the type of cells to be immobilized or types or concentrations of lectins used, and in general it is preferably 30 G or more, more preferably in a range of 100–400 G, and further preferably in a range up to 1,000 G.

More specifically, in the case in which, for example, PVLA is employed as the glycoconjugate polymer, and SBA or the like is employed as the galactose-specific lectin in order to recover desired hematopoietic cells from liquid and/or solid phase, then the ease of attachment goes in the order of mature erythrocytes, NRBC>leukocytes>immature CD34-positive cells. Accordingly, if the amount of lectin is reduced, the CD34-positive cells will first become unattached, and then the leukocytes will become unattached, and finally, the mature erythrocytes and NRBC will be the only cells which are selectively attached. In other words, if to the separation method of the present invention is conducted using an amount of added lectin such that only CD34-positive cells remain unattached, then the CD34-positive cells will be selectively contained in the liquid phase, and it will be possible to recover these CD34-positive cells with a high degree of purity. Furthermore, if the amount of added lectin is further reduced, and only mature erythrocytes and NRBCs are attached, then it is possible to selectively recover mature erythrocytes and NRBCs from the solid phase.

In this separation method of the present invention, it is also possible to remove granulocytes and leukocytes and the like from the blood sample obtained in advance prior to the first stage, so as to concentrate the desired cells. In such a case, multi-purpose high-density liquid set to specific gravity of about 1.077 such as Ficoll Paque, Histo Paque, Percall, or the like may be generally used, while in the present invention, those having a specific gravity of 1.085–1.10 are particularly used in a pretreatment for separating and concentrating NRBC from a blood sample. In practice, the present inventors confirmed that when a high-density liquid, such as Ficoll Paque, Histo Paque, Percall, or the like, having a specific gravity of 1.095 is used, the resulting recovered amounts of NRBC via lectin were unproved about 1.5 times larger than those obtained using a conventional high-density liquid having a specific gravity of 1.077. Although many investigators have considered the effects of these pretreatments for a long time, no conclusion has been obtained due to variations among individuals and the like. Therefore, the other conditions may also be appropriately employed in the selective separating method of the present invention.

Furthermore, as shown in FIG. 1, it is also of course possible to conduct the method in the same way using synthetic glycoconjugate polymer of glucose family and lectin.

In general, negative separation, in which cells other than those which are desired are immobilized, and positive separation, in which the cells which are desired are immobilized and concentrated, are known as methods for separating cells; however, the separation method of the present invention makes use of both negative and positive separation by appropriately adjusting the concentration of lectins.

In the selective separation of hematopoietic stem cells which are present in very small amounts, in order to reduce the number of the cells which are wasted, the method described above may be repeated a number of times to make it possible to increase the yield of the desired cells.

The blood sample which is separated and refined by means of the separation method of the present invention may be from any source, including peripheral blood; however, in the selective recovery of stem cells, bone marrow fluid, umbilical blood, or placental blood is preferable. Furthermore, in the selective recovery of NRBCs, umbilical blood or maternal blood is preferable.

EXAMPLES

Hereinbelow, a case will be concretely discussed in which, following the separation method of the present invention, and employing AZ-PVLA as a glycoconjugate polymer, and using a phosphate-buffered physiological saline (PBS) supplemented with 0.1% by weight of bovine serum albumin as a cell suspension. In this case, immature hematopoietic stem cells are selectively separated and recovered.

1: Incubation Conditions

Example 1

Temperature Effects (1)

First stage: Cord blood mononucleated cells monocytes were obtained as cells treated with ammonium chloride after centrifugation on Ficoll Paque. In a tube made by polypropylene, PBS containing a variety of concentrations of SBA (lectin specific for galactose) was added to a suspension of the mononucleated cells derived from cord blood of $2 \times 10^6$ cells per ml, and the mixture was incubated at a temperature of 4° C. for a period of 30 minutes and was gently stirred at intervals of 5 minutes.

Second stage: after the completion of the incubation described above, the suspension was transferred to a dish having a diameter of 35 mm which was coated with AZ-PVLA, the tube was further rinsed with 1 ml of the isotonic salt solution described above, and this rinse liquid was also added to the dish, and incubation was conducted at a variety of temperatures from 4° C. to 37° C. for a period of 60 minutes. Alternatively, the dish and cells were centrifuged for a predetermined period at 90 G in place of the incubation for 60 minutes, or the substrate and cells were incubated for 15 minutes and then centrifuged for a predetermined period in place of the incubation for 60 minutes. In addition, both of the centrifuging treatments were conducted concomitantly.

Third stage: after stirring, the suspension liquid was recovered, washing was conducted with 1 ml of the PBS, and the solid phase (dish) and liquid phase (suspended liquid) were separated.

The recovered cell count in the cellular suspension liquid obtained was measured using an automated blood cell counter, and the proportion (attachment ratio) of attaching cells with respect to the number of cells used was calculated. As a result, it was discovered that there was a trend for the attachment ratio to increase as the amount of lectin added increased at all temperatures. The amount of added lectin (SBA), which was minimally necessary in order to cause the adhesion of 80% of the mononucleated cells at each temperature, was as shown in Table 1 below.

TABLE 1

| Processing Temperature | Minimum Amount of Added SBA Required to Cause 80% of Mononucleated cell Attachment to applying $2 \times 10^6$ cells |
|---|---|
| 37° C. | 1.0 mg |
| 30° C. | 0.5 mg |
| 10° C. | 0.05 mg |
| 4° C. | 0.025 mg |

From these results, it can be seen that the amount of added lectin (SBA) necessary to cause the attachment of 80% of the mononucleated cells decreased along with a decrease in temperature, so that in other words, by reducing the incubation temperature, the attachment efficiency could be increased, so that attachment and separation became possible with small amounts of lectin. Under the processing temperature at 40° C., a cellular attachment of approximately 50% was observed at 0.01 mg. The fact that this cellular attachment was specific for carbohydrate via lectin was confirmed by the fact that, by adding the galactose solution in various concentrations to the dish, the cellular adhesion was inhibited by 60–90% both at 4° C. and 37° C.

In addition, in the case in which centrifuging at 90 G was conducted in place of the incubation for 60 minutes, centrifuging for not less than 3 minutes provided the same cell-attachment as that obtained by the incubation for 60 minutes. Furthermore, in the case in which incubation for 15 minutes followed by centrifuging at 90 G was conducted in place of the incubation for 60 minutes, stable cell-attachment was obtained by centrifuging for not less than 2 minutes. These centrifuging treatments were able to facilitate and stabilize the selective attachment of the cells via lectins and contributed to shortening processing period, unless such centrifuging was so excessive to destroy the cells resulting in unselective adhesion.

Example 2
Temperature Effects (2)

A procedure was followed under conditions which were identical to those of Example 1, with the exception that the lectins employed were PNA and ECL (both of which are galactose-specific), and the results shown in Table 2 below were obtained.

TABLE 2

| Lectin | Amount of Lectin Added (mg/2 × 10⁶ cells) | Cellular Attachment Ratio | |
|---|---|---|---|
| | | Processing Temperature 4° C. | Processing Temperature 37° C. |
| PNA | 0.72 | 73 | 44 |
| ECL | 0.02 | 81 | 58 |

From the results in Table 2, it became clear that, irrespective of the type of lectin employed, a relationship was present between the cellular attachment ratio and the incubation temperature, as shown above.

Example 3
Contents of Temperature Effects

The same type of experiment was conducted under conditions identical to those of the incubation at 37° C. in Example 1, and sodium azide was added to the cell suspension. The results are shown in Table 3. Here, the attachment of the cells is expressed in terms of the proportion of cells recovered which were not attached (the recovery ratio).

TABLE 3

| Incubation Conditions (Amount of SBA Added: 1 mg/2 × 10⁶ cells) | Recovery Ratio (%) |
|---|---|
| Incubation temperature of 37° C. | 14.8 |
| Incubation temperature of 37° C. + 10 mM sodium azide | 3.9 |
| Incubation Temperature of 4° C. | 6.7 |

From the results shown above, it can be seen that the cellular attachment via lectin increases with a decrease in temperature; however, this phenomenon is also observed if sodium azide, which is known to suppress metabolic activities, is added even if the temperature is not reduced. That is to say, the temperature-dependent affinity of the lectin for the cells is affected by the cells affected by the cellular membrane mobility, and a tendency is observed for the affinity to increase as the membrane mobility decreases.

2. Selective Affinity

Example 4
Selective Affinity Based on the Maturity of Leukocytes

Immature leukocytes express a surface marker termed CD34 on the surface thereof (they are CD34-positive) and are known to become CD34-negative as they mature. Conventionally, the selective immobilizing of immature cells was conducted using CD34 antibodies. Here, on solid surfaces with PVLA having a β-bond galactose terminus attached (at incubation temperatures of 4° C. and 37° C.), and PVMeA having an α-bond galactose terminus attached (at an incubation temperature of 4° C.), selective attachment was investigated using various amounts of added lectin. The results thereof are shown in Table 4. The described values of SBA in the table represent the amount added with respect to $2 \times 10^6$ cells

TABLE 4

| Leukocyte Maturity | Cellular Attachment Ratio (%) | | |
|---|---|---|---|
| | SBA 0.025 mg PVMeA (4° C.) | SBA 0.05 mg PVLA (4° C.) | SBA 1 mg PVLA (37° C.) |
| Immature, CD34-positive cells | 20 | 15 | 12 |
| Mature, CD34-negative cells | 76 | 73 | 70 |

From the results above, it was discovered that by means of the separation method of the present invention using lectin, it is possible to selectively separate CD34-positive immature cells and CD34-negative mature cells. Moreover, by means of setting the incubation temperature to a low temperature, the amount of added lectin required was reduced to approximately 1/20 of that formerly required. Furthermore, when PVMeA was employed as the glycoconjugate polymer, in comparison with the case in which PVLA was employed, selective attachment was obtained even when the amount of added lectin was further reduced.

It is generally known that SBA has a stronger affinity to galactose of α-bond type. Therefore, the results, in which the selective cell attachment to PVMeA having α-bond type galactose terminal was observed at lower lectin concentration, demonstrate that the separating method of the present inventors is based on quite specific affinity of lectins. Furthermore, the present method clarified that the low-temperature-incubation is an effective process which can strongly enforce the affinity of lectins.

Example 5
Selective Affinity among Blood Cells

An experiment was conducted which was identical to that of Example 1 and the incubation temperature was set at 4° C., and the amount of added lectin required to cause the attachment of 95% of erythrocytes and of leukocytes derived from umbilical cord blood was determined. In this case, the hemolysis was not conducted. The results thereof are shown in Table 5 below.

TABLE 5

| Cells | Amount of Added Lectin Required to Cause 95% or more of Erythrocytes or Leukocytes to Attach (2 × 10⁶ cells) |
|---|---|
| Leukocytes | 300 micrograms or more |
| Erythrocytes | 50 micrograms or more |

As shown in Table 5, in comparing the attachment via lectin of the erythrocytes and leukocytes, the erythrocytes showed higher affinity, and were capable of attachment at lower levels of added lectin.

Example 6
Separation of Umbilical Cord Blood Erythroblasts

The incubation temperature was set to 4° C., and the amount of lectin (SBA) added was altered to a very small amount of 50 micrograms or less per 2×10⁶ cells, and the cells attaching to a dish covered with PVLA were investigated as in Example 5. In addition, the results obtained by centrifuging the dish and attached cells at 450 G after separating the solid phase from liquid phase in the third step were compared.

Figure 2:
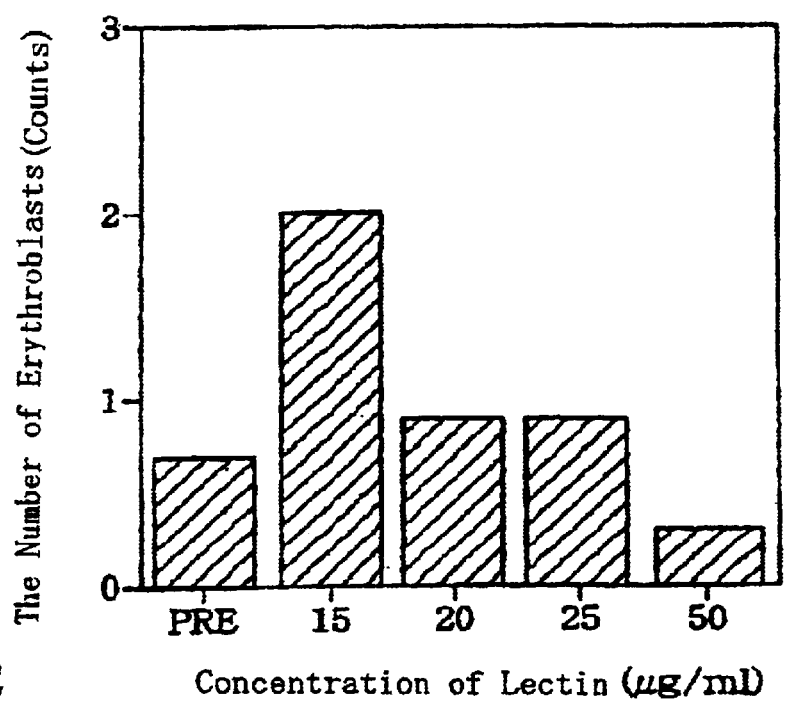
FIG. 2 is a graph showing the results of the selective concentration of erythroblasts by means of changes in the lectin concentration in Example 6.

The method employed in this investigation was such that the attaching cells were allowed to dry on the dish, cells were then stained with hematoxylin and erythrosin, and positively stained erythroblasts were counted, and 100 cells in a randomly selected area were counted and the number of erythroblasts contained therein was evaluated. The results thereof are shown in FIG. 2. In the figure, PRE indicates a comparative example in which a large amount (300 micrograms) of lectin was added and almost all cells were caused to attach.

If the amount of lectin added is decreased, and the attachment of leukocytes which have a lower affinity for the lectin is preferentially reduced, then mature erythrocytes and erythroblasts are selectively caused to attach to the dish. Accordingly, it is possible to detect erythroblasts which are present at low levels in umbilical cord blood, at a high probability of 1 or more/100 cells. Furthermore, when centrifuging at 450 G for not less than 3 minutes was conducted after separating the solid phase from liquid phase, the attached cells exhibited uniform spherical shapes which provided good staining sensitivity and therefore made it easy to visually recognize erythroblasts with a microscope. However, when the centrifuging treatment was not sufficient (for example, in a case wherein centrifuging force was too small or centrifuging period was too short), uniform cell staining image could not be obtained which resulted in difficulties in visual recognition of desired cells with a microscope. Accordingly, it was found that it is very important to centrifuging the cells attached to the substrate with appropriate conditions when one intends to improve the efficacy of a cytological examination, which requires detection of fine nucleus structure by cell staining.

Example 7
Concentration of Fetal Erythroblasts in the Maternal Blood

Following the method of Example 6, a cell fraction separated by the Ficoll Paque was recovered from maternal blood, 10 micrograms of a lectin (SBA) was added with respect to 2×10⁶ cells, and this was incubated for a period of 30 minutes at a temperature of 18° C. in a PVMeA-covered separable slide chamber. For the purposes of comparison, a case was also evaluated in which the amount of lectin added was 300 micrograms. The experimental results for 20 examples are shown in Table 6 below.

TABLE 6

| Number of Positively Stained Erythroblasts Adhered to the Dish | Amount of Lectin Added | |
|---|---|---|
| | 10 micrograms | 300 micrograms |
| 0–1 | 1 instance | 19 instances* |
| 2–5 | 3 instances | 1 instance* |
| 6–10 | 7 instances | — |
| 11–30 | 8 instances | — |
| 31 or more | 1 instance | — |

When 300 micrograms was added, too many nucleated leukocytes other than erythroblasts were caused to attach, so that a miss count occurred.

In consideration with the above results, the optimal amounts of lectin (SBA) to be added for detecting fetal erythroblasts were estimated. The results estimated from 20 instances are indicated in the following Table 7. In each case, a maternal body was examined based on informed consent by echo imaging to ascertain that she carries healthy boy. The erythroblasts separated from the collected maternal blood were examined by FISH assay using Aneu Vysion Assay Kit (VYSIS, INC.) to detect a Y-probe.

TABLE 7

| The Amount of Lectin Added ($\mu$g) | 2 | 4 | 8 | 12 | 16 |
|---|---|---|---|---|---|
| The Number of NRBC detected (relative value when the number of NRBC detected with 8 $\mu$g of lectin is assumed as 1.00) | 0 | 0.16 | 1.00 | 1.07 | 0.97 |

These results show that when the amount of lectin added is decreased and the attachment of leukocytes is reduced, it is possible to selectively accumulate erythroblasts, and it is possible to efficiently detect erythroblasts, which are useful in genetic diagnosis, from maternal blood. In addition, it was found that there was an apparent lower-limit of the amount of lectin to be added, and that the loss of erythroblasts was reduced when 8 $\mu$g or more of lectin was added. In such cases, contamination with nucleated cells or leukocyte was gradually increased when the amount of lectin exceeded 20 $\mu$g, the contamination occurred so abundantly that the recognition of NRBC became difficult when the amount of lectin reached to 32 $\mu$g or more. Furthermore, these results were reproducible when PVLA was employed as the glycoconjugate polymer.

On the other hand, with the maternal blood samples containing small amounts of erythrocyte components such as erythroblasts, good erythrocyte selective attachment was reproduced without the incubation with lectin at the first stage.

Furthermore, 8 samples of maternal bodies who carries a boy were examined at this time, and Y-probes specific for boy were detected in the 8 samples which means that fetal cells can be recovered from maternal blood with high yield. Therefore, it was found that the separation method for nucleated erythroblasts using a lectin of the invention is an effective means for detecting fetal cells from maternal blood with no- or low-invasion and examining the fatal chromosomes.

The fractions of CD34-positive cells concentrated in accordance with Example 4 were recovered, and their colony-forming abilities were compared using commercially available assay kit (MethoCult GF H4434, Stem Cell Technologies Inc.). As a result, the CD34-positive cells concentrated by the separation method via lectin of the invention exhibited colony-forming abilities of 8.8 times larger than that obtained without such separation. These results demonstrate that the treatment with lectin can effectively increase the hematopoietic cells without affecting their subsequent colony-forming abilities. Accordingly, it is believed that the cell separating method of the invention can provide a transplant graft with reduced lymphocyte, which can alleviate GVHD, to a patient in need of stem cell transplant, and therefore, the separating method of the invention can be used in effective detection of oncogenes derived in each stage of differentiation of leukemia cells.

Industrial Applicability

As described in detail above, the separation method and separation apparatus of the present invention are based on interaction among cells-lectins and glycoconjugate polymers-lectins. In greater detail, the present invention utilizes the fact that the changes in attachment properties depending on the state of activity of cells or the amount of lectin added, and changes in attachment selectivity depending of the type of cells were observed in the above interactions. By employing the separation method and separation apparatus of the present invention, it is possible to selectively separate and recover cells which have great clinical significance, such as hematopoietic stem cells or NRBCs.

What is claimed is:

1. A method for selectively separating and recovering hematopoietic cells and/or erythroblasts from a blood sample containing differentiated mature cells, immature hematopoietic cells and erythroblasts, characterized in that the method comprises the following steps:

(1) a step for causing said sample to interact with lectins to form cell-lectin complexes/non-complexes under conditions in which the cells are rendered inactive, (2) a step for incubating a sample containing said cell-lectin complexes/non-complexes under said conditions with a substrate, the surface of which is covered with a synthetic glycoconjugate polymer having carbohydrate moieties specifically recognized by said lectins, and immobilizing said cells on the surface of said substrate via lectins, and (3) a step for separating the liquid phase from the solid phase, and recovering desired blood cells from said liquid phase and/or said solid phase;

and in that said lectins are present in an amount such that they bind to the cells recovered from said solid phase and immobilize these cells on the surface of the substrate, but do not immobilize the cells recovered from said liquid phase to the surface of said substrate.

2. A method according to claim 1, characterized in that said method further comprises:

(4) a step for accelerating and stabilizing the immobilization of cells by centrifuging said substrate and cells simultaneously prior to or after the incubation or a step for stabilizing the immobilization of cells by centrifuging the substrate on which the cells are immobilized during the recovering step.

3. A method according to claim 1 or 2, characterized in that said conditions under which said cells are rendered inactive are:

low temperature conditions of 0° C. or above but less that 37° C., or conditions in which a pharmaceutical agent is added which suspends cellular respiration.

4. A method according to claim 1 or 2, characterized in that the concentration of said lectins is within a range of 20 mg/ml or less per cell.

5. A method according to claim 1 or 2, characterized in that the incubation period of step (1) is set within a range of 0–120 minutes, and the incubation period of step (2) is set to a range of 10–120 minutes.

6. A method according to claim 1, characterized in that said substrate is selected from a group consisting of dishes, flasks, plates, cuvettes, films, fibers, or beads made of glass, polystyrene, polycarbonate, polysulfone, polyurethane, or vinyl copolymer.

* * * * *

UNITED STATES PATENT AND TRADEMARK OFFICE
CERTIFICATE OF CORRECTION

PATENT NO. : 6,926,915 B1
DATED : August 9, 2005
INVENTOR(S) : Hirofumi Yura et al.

It is certified that error appears in the above-identified patent and that said Letters Patent is hereby corrected as shown below:

Column 7,
Line 37, delete "unproved", and insert -- improved --.

Signed and Sealed this

Twenty-eighth Day of March, 2006

JON W. DUDAS
*Director of the United States Patent and Trademark Office*